(12) United States Patent
Michihata

(10) Patent No.: US 11,322,245 B2
(45) Date of Patent: May 3, 2022

(54) MEDICAL IMAGE PROCESSING APPARATUS AND MEDICAL OBSERVATION SYSTEM

(71) Applicant: Sony Olympus Medical Solutions Inc., Tokyo (JP)

(72) Inventor: Taihei Michihata, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 65 days.

(21) Appl. No.: 16/503,737

(22) Filed: Jul. 5, 2019

(65) Prior Publication Data
US 2020/0020436 A1    Jan. 16, 2020

(30) Foreign Application Priority Data

Jul. 13, 2018    (JP) .............................. JP2018-133374

(51) Int. Cl.
| | |
|---|---|
| *G06T 7/00* | (2017.01) |
| *G16H 30/40* | (2018.01) |
| *A61B 5/00* | (2006.01) |
| *A61B 1/00* | (2006.01) |
| *A61B 1/06* | (2006.01) |
| *A61B 1/04* | (2006.01) |

(52) U.S. Cl.
CPC ......... *G16H 30/40* (2018.01); *A61B 1/00009* (2013.01); *A61B 5/0071* (2013.01); *G06T 7/0012* (2013.01); *A61B 1/04* (2013.01); *A61B 1/0638* (2013.01); *G06T 2207/10064* (2013.01); *G06T 2207/30096* (2013.01)

(58) Field of Classification Search
None
See application file for complete search history.

(56) References Cited

U.S. PATENT DOCUMENTS

| | | | |
|---|---|---|---|
| 2006/0108509 A1* | 5/2006 | Frangioni | A61B 5/415 250/208.1 |
| 2006/0167357 A1* | 7/2006 | Lauritsch | A61B 5/444 600/431 |
| 2006/0178565 A1* | 8/2006 | Matsui | G01N 21/6456 600/160 |
| 2007/0073159 A1* | 3/2007 | Ehben | A61B 5/0059 600/473 |

(Continued)

FOREIGN PATENT DOCUMENTS

| | | | |
|---|---|---|---|
| JP | 2016-022325 A | 2/2016 | |
| WO | WO-2018146979 A1 * | 8/2018 | ............. G09G 5/377 |

*Primary Examiner* — Jiangeng Sun
(74) *Attorney, Agent, or Firm* — Xsensus, LLP

(57) ABSTRACT

A medical image processing apparatus includes: a superimposed image generation unit configured to generate a superimposed image by superimposing a subject image and a fluorescent image in areas corresponding to each other; a determination unit configured to determine whether or not at least one of a subject and an observation device moves from timing before timing at which one of the subject image and the fluorescent image is captured to the timing; and a superimposition controller configured to cause the superimposition image generation unit to prohibit a superimposition in an area of at least a part of the subject image and the fluorescent image when the determination unit determines that at least one of the subject and the observation device moves.

19 Claims, 9 Drawing Sheets

(56) References Cited

U.S. PATENT DOCUMENTS

| | | | | |
|---|---|---|---|---|
| 2009/0266999 | A1* | 10/2009 | Krattiger | G02B 23/2446 250/459.1 |
| 2012/0013773 | A1* | 1/2012 | Yoshino | G06T 7/32 348/241 |
| 2012/0257034 | A1* | 10/2012 | Shimokita | A61B 5/0059 348/77 |
| 2015/0276602 | A1* | 10/2015 | Ishihara | A61B 1/0638 250/458.1 |
| 2017/0319051 | A1* | 11/2017 | Kuriyama | A61B 1/045 |

* cited by examiner

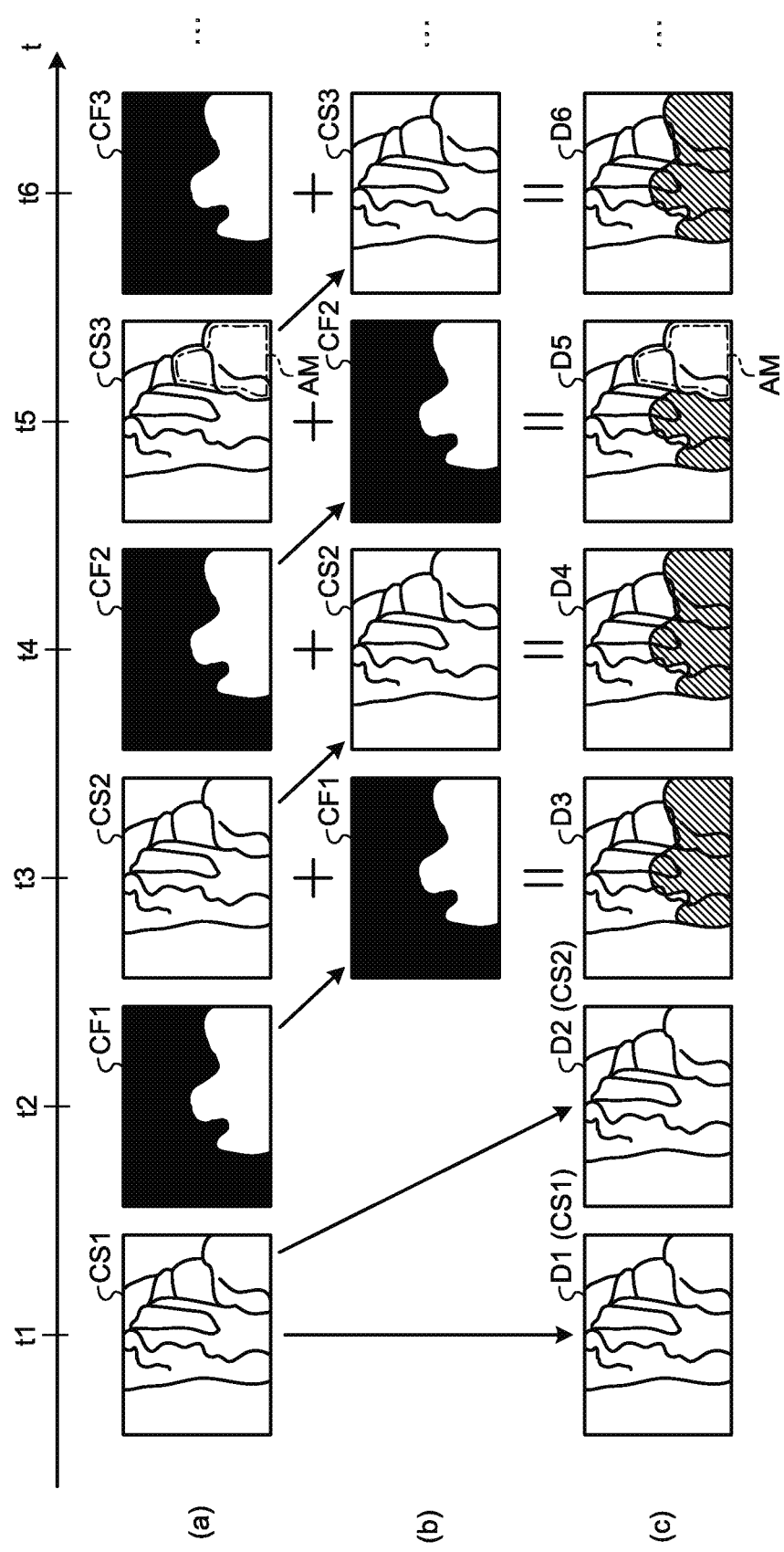

MEDICAL IMAGE PROCESSING APPARATUS AND MEDICAL OBSERVATION SYSTEM

CROSS-REFERENCE TO RELATED APPLICATION

The present application claims priority to and incorporates by reference the entire contents of Japanese Patent Application No. 2018-133374 filed in Japan on Jul. 13, 2018.

BACKGROUND

The present disclosure relates to a medical image processing apparatus and a medical observation system.

In the related art, a medical image processing apparatus which captures an image of a subject to generate a subject image and a fluorescent image, and is connected to an observation device has been known (for example, see JP 2016-022325 A).

Here, the subject image is an image obtained by irradiating the subject with white light or the like and capturing a subject image reflected from the subject. Further, the fluorescent image is an image obtained by irradiating the subject with near-infrared excitation light or the like, exciting a drug accumulated in a lesion part in the subject, and capturing the fluorescent image emitted from the subject.

Then, the medical image processing apparatus (image processing processor) described in JP 2016-022325 A acquires the subject image and the fluorescent image from the observation device (an insertion unit and an imaging unit), and generates a superimposed image by superimposing the subject image and the fluorescent image in areas corresponding to each other. The superimposed image is displayed on a display device. A doctor recognizes the lesion part by checking the superimposed image displayed on the display device, and treats the lesion part.

SUMMARY

When timing at which the subject image is imaged (hereinafter, referred to as first timing) and timing at which the fluorescent image is imaged (hereinafter, referred to as second timing) are different from each other, the subject or the observation device moves, such that the subject at the first timing and a position of the observation device and the subject at the second timing and the position of the observation device are different from each other.

In such a case, the corresponding observed regions of the subject image and the fluorescent image are shifted from each other. For this reason, there is a possibility that a doctor may recognize, as a lesion part, a site at which no lesion part is actually present, from the superimposed image displayed on the display device. That is, there is a problem in that the convenience may not be improved.

According to one aspect of the present disclosure, there is provided a medical image processing apparatus connected to an observation device that generates a subject image by capturing the subject image reflected from a subject and generates a fluorescent image by capturing a fluorescent image emitted from the subject at different timing from the subject image, the medical image processing apparatus including: a superimposed image generation unit configured to generate a superimposed image by superimposing the subject image and the fluorescent image in areas corresponding to each other; a determination unit configured to determine whether or not at least one of the subject and the observation device moves from timing before timing at which one of the subject image and the fluorescent image is captured to the timing; and a superimposition controller configured to cause the superimposition image generation unit to prohibit a superimposition in an area of at least a part of the subject image and the fluorescent image when the determination unit determines that at least one of the subject and the observation device moves.

According to another aspect of the present disclosure, there is provided a medical image processing apparatus connected to an observation device that generates a subject image by capturing the subject image reflected from a subject and generates a fluorescent image by capturing a fluorescent image emitted from the subject at different timing from the subject image, the medical image processing apparatus including: a superimposed image generation unit configured to generate a superimposed image by superimposing the subject image and the fluorescent image in areas corresponding to each other; a determination unit configured to determine whether or not at least one of the subject and the observation device moves from timing before timing at which at least one of the subject image and the fluorescent image is captured to the timing; and a notification controller configured to notify a notification device of information indicating the motion when the determination unit determines that at least one of the subject and the observation device moves.

BRIEF DESCRIPTION OF THE DRAWINGS

FIG. 9 is a diagram illustrating a concrete example of an image displayed on a display device.

DETAILED DESCRIPTION

Figure 1:
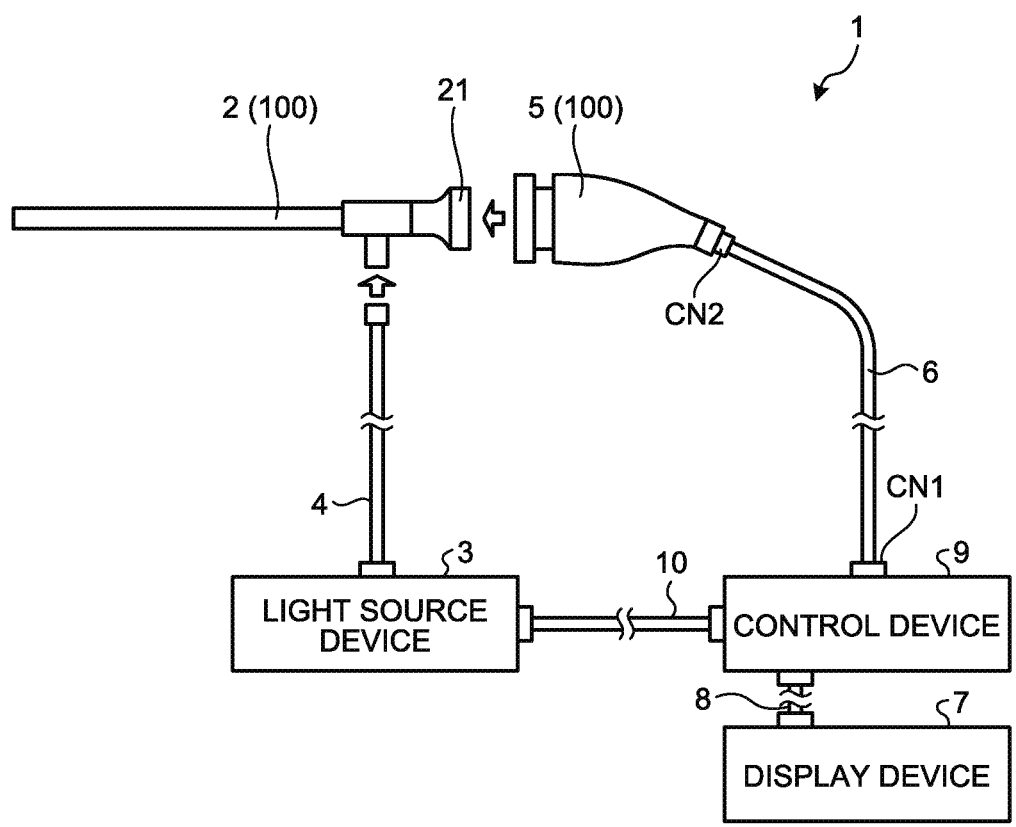
FIG. 1 is a diagram illustrating a configuration of a medical observation system according to a first embodiment.

Hereinafter, a mode (hereinafter, "embodiment") for carrying out the present disclosure will be described with reference to the drawings. It is to be noted that the present disclosure is not limited to embodiments to be described below. Further, in the description of the drawings, the same reference numerals are attached to the same parts.

First Embodiment

Schematic Configuration of Medical Observation System

FIG. 1 is a diagram illustrating a configuration of a medical observation system 1 according to a first embodiment.

The medical observation system 1 is used in medical fields and is a system for observing a subject such as an inside of a living body. As illustrated in FIG. 1, the medical observation system 1 includes an insertion unit 2, a light source device 3, a light guide 4, a camera head 5, a first transmission cable 6, a display device 7, a second transmission cable 8, a control device 9, and a third transmission cable 10.

In the first embodiment, the insertion unit 2 is constituted by a rigid endoscope. That is, the insertion unit 2 has an elongated shape, in which the whole thereof is rigid, or a part thereof is soft and the other part thereof is rigid, and is inserted into a living body. The insertion unit 2 is provided with an optical system which is constituted by one lens or a plurality of lenses and condenses light (subject image or fluorescent image) from a subject.

The light source device 3 is connected to one end of the light guide 4, and supplies light for illuminating the inside of the living body, to one end of the light guide 4 under the control of the control device 9. In the first embodiment, the light source device 3 includes an LED that emits white light (normal light) and a semiconductor laser that emits near-infrared excitation light in a near-infrared wavelength region. Then, under the control of the control device 9, the light source device 3 alternately supplies white light and near-infrared excitation light in a time division manner as light for illuminating the inside of the living body. In the first embodiment, the light source device 3 is configured separately from the control device 9, but the first embodiment is not limited thereto, and a configuration provided inside the control device 9 may be adopted.

One end of the light guide 4 is detachably connected to the light source device 3 and the other end of the light guide 4 is detachably connected to the insertion unit 2. The light guide 4 transmits light (white light or near-infrared excitation light) supplied from the light source device 3 from one end to the other end and supplies the light to the insertion unit 2. The light supplied to the insertion unit 2 is emitted from a distal end of the insertion unit 2 and irradiated into a living body. When the white light is irradiated to the living body, the subject image reflected from the living body is condensed by the optical system in the insertion unit 2. In addition, when the near-infrared excitation light is irradiated to the living body, a drug such as indocyanine green accumulated in a lesion part in the living body is excited, and a fluorescent image emitted from the living body is condensed by the optical system in the insertion unit 2

The camera head 5 is detachably connected to a proximal end (eyepiece portion 21 (FIG. 1)) of the insertion unit 2. The camera head 5 captures the subject image or the fluorescent image condensed by the insertion unit 2 under the control of the control device 9, and outputs an image signal (RAW signal) by the capturing. The image signal is, for example, an image signal of 4 K or more.

A detailed configuration of the camera head 5 will be described below.

The insertion unit 2 and the camera head 5 described above correspond to an observation device 100 (FIG. 1).

One end of the first transmission cable 6 is detachably connected to the control device 9 via a connector CN1 (FIG. 1), and the other end thereof is detachably connected to the camera head 5 via a connector CN2 (FIG. 1). The first transmission cable 6 transmits the image signal or the like output from the camera head 5 to the control device 9 and transmits a control signal, a synchronization signal, a clock, power and the like, which are output from the control device 9, to the camera head 5.

The image signal or the like from the camera head 5 to the control device 9 via the first transmission cable 6 may be transmitted as an optical signal or an electrical signal. The transmission of the control signal, the synchronization signal, and the clock from the control device 9 to the camera head 5 via the first transmission cable 6 is also the same.

The display device 7 is constituted by a display using a liquid crystal or organic electro Luminescence (EL) or the like, and displays an image based on a video signal from the control device 9 under the control of the control device 9.

One end of the second transmission cable 8 is detachably connected to the display device 7 and the other end of the second transmission cable 8 is detachably connected to the control device 9. The second transmission cable 8 transmits the video signal processed by the control device 9 to the display device 7.

The control device 9 corresponds to the medical image processing apparatus. The control device 9 is configured to include a central processing unit (CPU) and the like, and collectively controls the operation of the light source device 3, the camera head 5, and the display device 7.

A detailed configuration of the control device 9 will be described below.

One end of the third transmission cable 10 is detachably connected to the light source device 3 and the other end thereof is detachably connected to the control device 9. The third transmission cable 10 transmits the control signal from the control device 9 to the light source device 3.

Configuration of Camera Head

Next, a configuration of the camera head 5 will be described.

Figure 2:
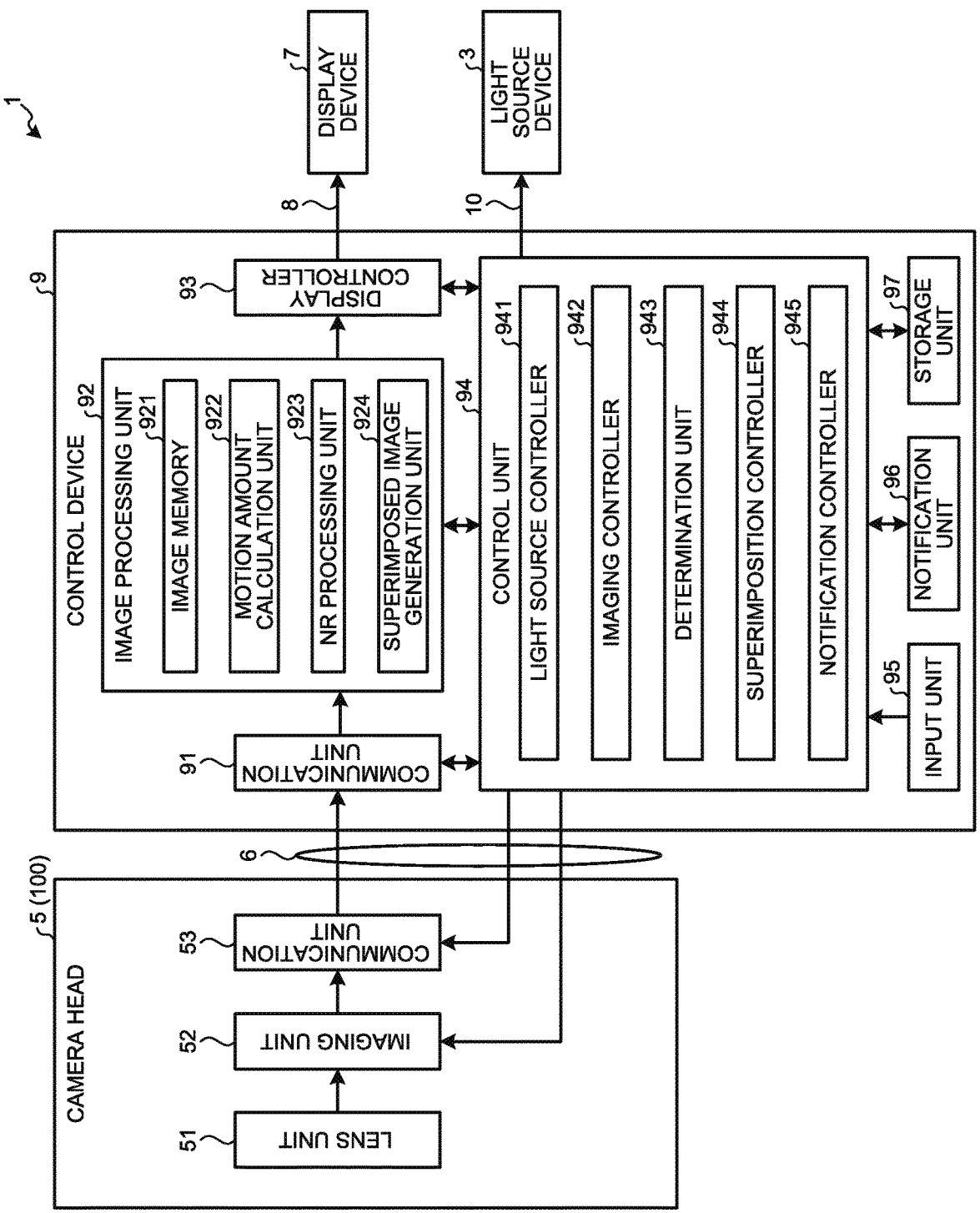
FIG. 2 is a block diagram illustrating a configuration of a camera head and a control device.

FIG. 2 is a block diagram illustrating a configuration of the camera head 5 and the control device 9.

In FIG. 2, for convenience of explanation, the connectors CN1 and CN2 between the control device 9 and the camera head 5 and the first transmission cable 6, and connectors between the control device 9 and the display device 7 and the second transmission cable 8, and connectors between the control device 9 and the light source device 3 and the third transmission cable 10 are not illustrated.

The camera head 5 includes a lens unit 51, an imaging unit 52, and a communication unit 53, as illustrated in FIG. 2.

The lens unit 51 is configured using one lens or a plurality of lenses, and forms the subject image or the fluorescent image condensed by the insertion unit 2 on an imaging surface of the imaging unit 52.

The imaging unit 52 captures the subject image or the fluorescent image under the control of the control device 9. Although not specifically illustrated, the imaging unit 52 includes an image sensor such as a charge coupled device (CCD) or a complementary metal oxide semiconductor (CMOS) that receives the subject image or the fluorescent image formed by the lens unit 51 and converts the subject image or the fluorescent image into an electrical signal (analog signal) and a signal processing unit that performs signal processing on the electrical signal (analog signal) from the image sensor to output the image signal (RAW signal (digital signal)).

The communication unit 53 functions as a transmitter that transmits the image signal (RAW signal (digital signal)) output from the imaging unit 52 to the control device 9 via the first transmission cable 6. The communication unit 53 is constituted by, for example, a high-speed serial interface that performs communication on an image signal with the control device 9 at a transmission rate of 1 Gbps or more via the first transmission cable 6.

Configuration of Control Device

Next, a configuration of the control device 9 will be described with reference to FIG. 2.

As illustrated in FIG. 2, the control device 9 includes a communication unit 91, an image processing unit 92, a display controller 93, a control unit 94, an input unit 95, a notification unit 96, and a storage unit 97.

The communication unit 91 functions as a receiver that receives the image signal (RAW signal (digital signal)) output from the camera head 5 (communication unit 53) via the first transmission cable 6. The communication unit 91 is constituted by, for example, a high-speed serial interface that performs communication on an image signal with the communication unit 53 at a transmission rate of 1 Gbps or more.

The image processing unit 92 processes the image signal (RAW signal (digital signal)) that is output from the camera head 5 (communication unit 53) and received by the communication unit 91 under the control of the control unit 94. As illustrated in FIG. 2, the image processing unit 92 includes an image memory 921, a motion amount calculation unit 922, a noise reduction (NR) processing unit 923, and a superimposed image generation unit 924.

The image memory 921 sequentially stores an image signal (RAW signal (digital signal)), which is output from a camera head 5 and received by a communication unit 91, for each frame by a predetermined number of frames. That is, the image signal (captured image for a predetermined number of frames) corresponding to a predetermined number of frames stored in the image memory 921 is sequentially rewritten to the captured image newly captured by the camera head 5.

In the following, for convenience of explanation, among the captured images captured by the camera head 5 (imaging unit 52), a captured image obtained by capturing a subject image is described as a subject image, and a captured image obtained by capturing a fluorescent image is described as a fluorescent image.

The motion amount calculation unit 922 performs first and second motion amount calculation processing.

Here, in the first motion amount calculation processing, a subject image (hereinafter, referred to as a current subject image) which is output from the camera head 5 and received by the communication unit 91 is stored in the image memory 921, and a subject image (hereinafter, referred to as an immediately previous subject image) captured by the camera head 5 two frames before is assumed as a first processing target. Here, when among the subject image and the fluorescent image alternately captured by the camera head 5, only the subject image is viewed, the immediately previous subject image is the subject image immediately before the current subject image in time series. That is, the first processing target is two subject images consecutive in time series. Then, in the first motion amount calculation processing, the motion amount (hereinafter, referred to as a first motion amount) from the immediately previous subject image is calculated for each region (each pixel in the first embodiment) in the current subject image.

In addition, in the second motion amount calculation processing, a fluorescent image (hereinafter, referred to as a current fluorescent image) which is output from the camera head 5 and received by the communication unit 91 and a fluorescent image (hereinafter, referred to as an immediately previous fluorescent image) which is stored in the image memory 921 and captured by the camera head 5 two frames before are assumed as a second processing target. Here, when among the subject image and the fluorescent image alternately captured by the camera head 5, only the fluorescent image is viewed, the immediately previous fluorescent image is the fluorescent image immediately before the current fluorescent image in time series. That is, the second processing target is two fluorescent images consecutive in time series. Then, in the second motion amount calculation processing, the motion amount (hereinafter, referred to as a second motion amount) from the immediately previous fluorescent image is calculated for each area (each pixel in the first embodiment) in the current fluorescent image.

Then, the motion amount calculation unit 922 outputs signals corresponding to the first and second motion amounts to the control unit 94.

Figure 3:
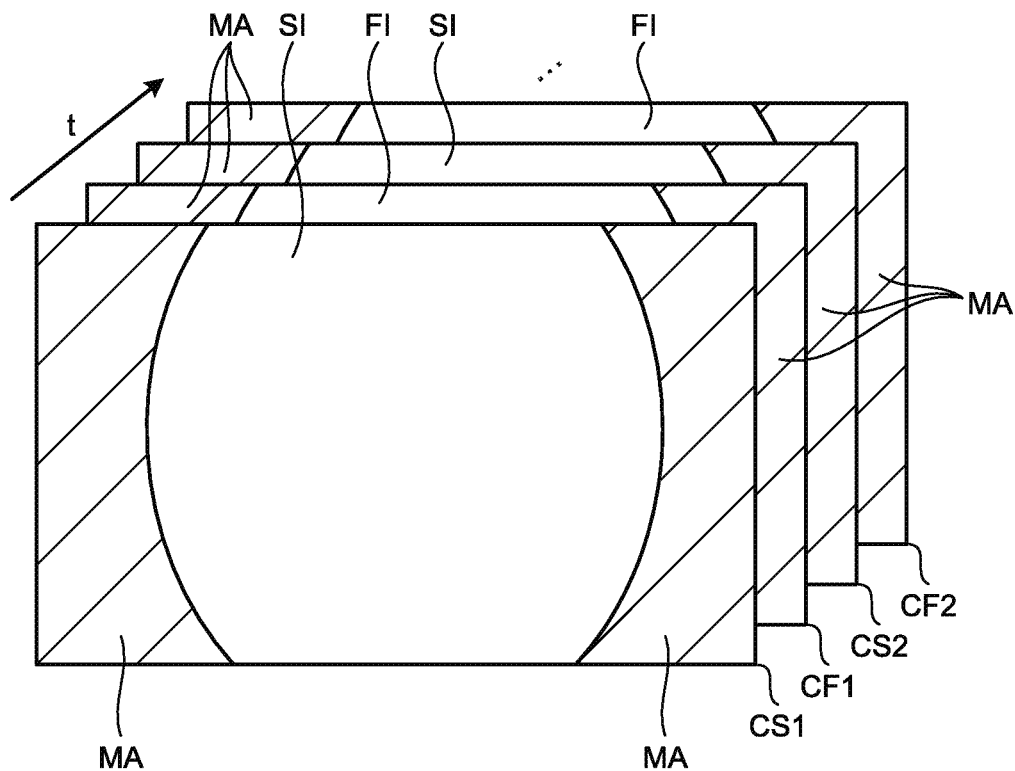
FIG. 3 is a diagram illustrating an example of first and second motion amount calculation processing.
Figure 4:
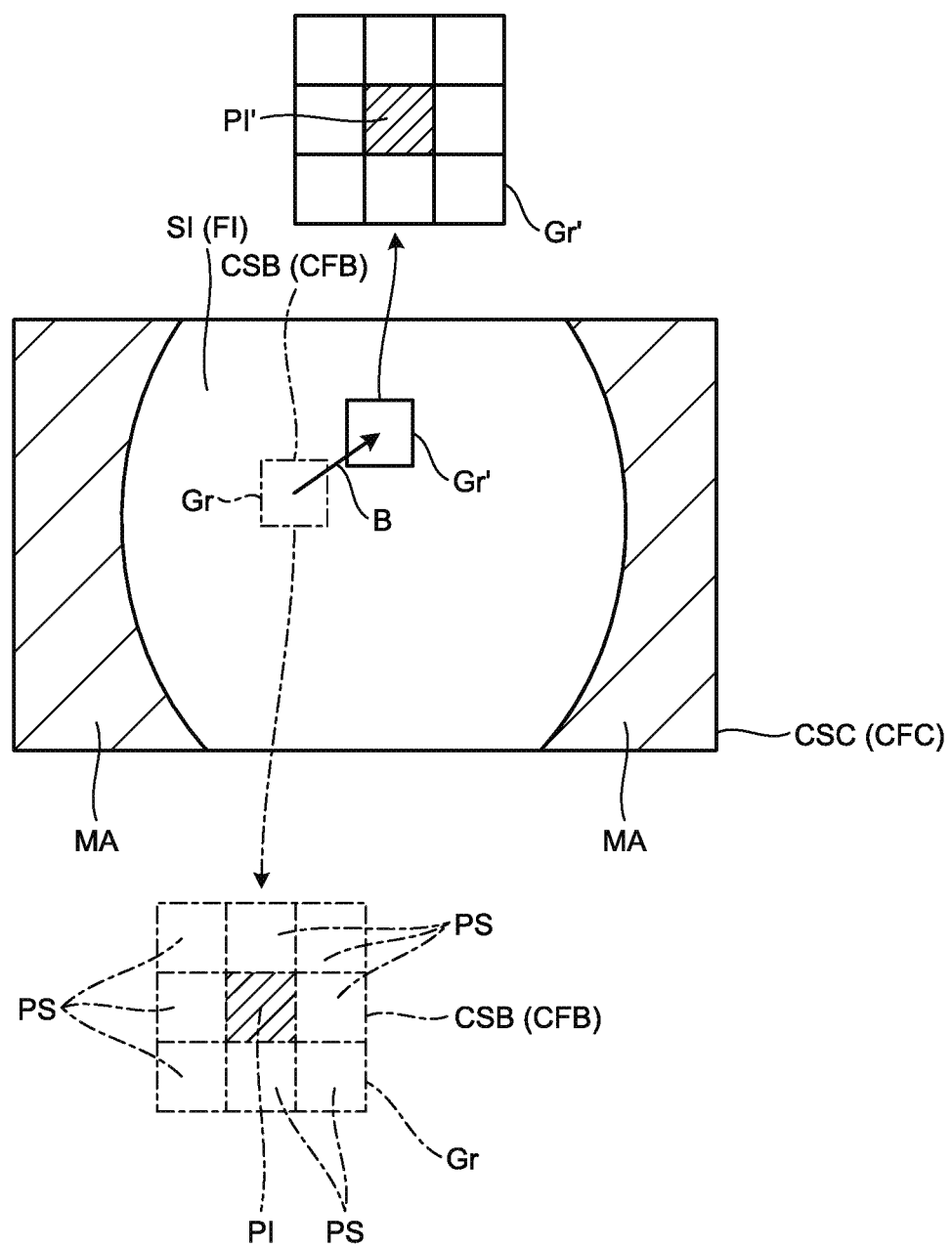
FIG. 4 is a diagram illustrating an example of the first and second motion amount calculation processing.
Figure 5:
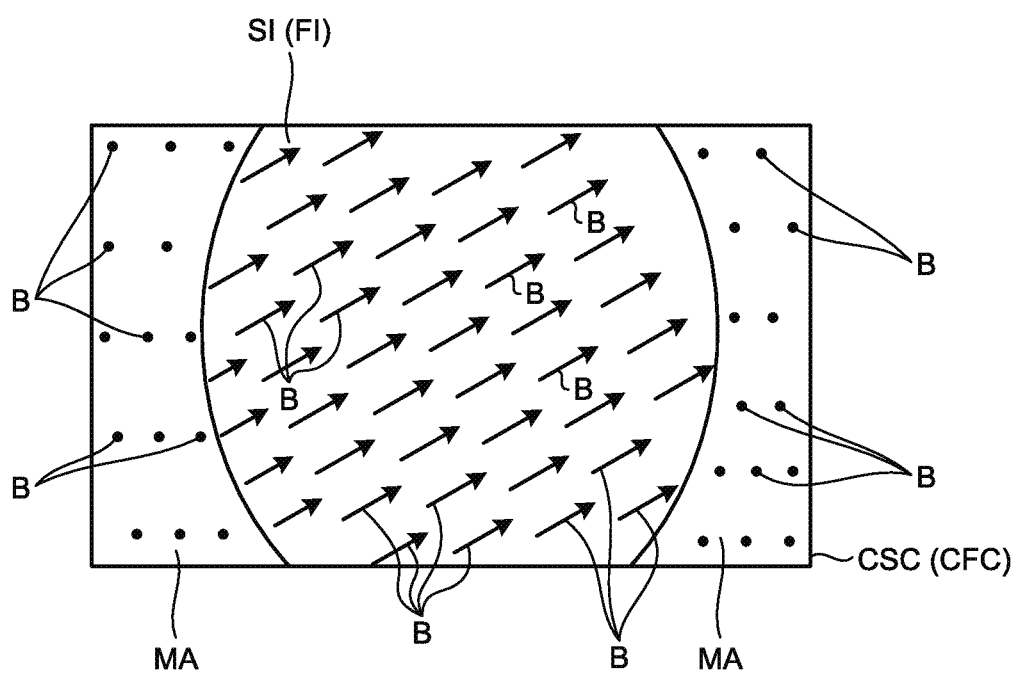
FIG. 5 is a diagram illustrating an example of the first and second motion amount calculation processing.

FIGS. 3 to 5 are diagrams for describing an example of the first and second motion amount calculation processing. Specifically, FIG. 3 is a diagram in which subject images CS1 and CS2 and fluorescent images CF1 and CF2 alternately captured by the camera head 5 are arranged in time series (in the direction of the arrow t). Here, light (a subject image or a fluorescent image) condensed in the insertion unit 2 has a substantially circular cross section. Therefore, a subject image SI in the subject images CS1 and CS2 has a substantially circular shape as illustrated in FIG. 3. The same goes for a fluorescent image FI in the fluorescent images CF1 and CF2. That is, the subject images CS1 and CS2 include the subject image SI and a mask area MA (represented by oblique lines in FIGS. 3 and 4) other than the subject image SI. Similarly, the fluorescent images CF1 and CF2 include the fluorescent image FI and the mask area MA other than the fluorescent image FI. In addition, FIGS. 4 and 5 are diagrams corresponding to FIG. 3 and illustrate a current subject image CSC (current fluorescent image CFC).

For example, as illustrated in FIGS. 4 and 5, the motion amount calculation unit 922 executes the first and second motion amount calculation processing using a block matching method.

Specifically, the motion amount calculation unit 922 executes the first motion amount calculation processing using the block matching method as described below.

The motion amount calculation unit 922 selects a pixel of interest PI (FIG. 4) among all pixels in an immediately previous subject image CSB (FIG. 4). In addition, the motion amount calculation unit 922 selects a pixel group Gr (FIG. 4) that includes the pixel of interest PI and a plurality of surrounding pixels PS (FIG. 4) located around the pixel of interest PI. In the example of FIG. 4, the number of surrounding pixels PS is eight (the number of pixel groups Gr is nine of 3×3), but the number is not limited to eight, and other numbers (for example, the number of surrounding pixels PS may be 24 (the number of pixel groups Gr is 25 of 5×5)).

Next, the motion amount calculation unit 922 specifies a pixel group Gr' (FIG. 4) having the highest correlation with the pixel group Gr over the entire region of the current subject image CSC. Then, the motion amount calculation unit 922 calculates, as a motion vector B (FIG. 4) of a pixel of interest PI', a vector from the pixel of interest PI located at the center of the pixel group Gr in the immediately previous subject image CSB to the pixel of interest PI' located at the center of the pixel group Gr' in the current subject image CSC.

The motion amount calculation unit 922 sequentially executes the processing described above while changing the pixel of interest PI for all the pixels in the immediately previous subject image CSB, and as a result, as illustrated in FIG. 5, the motion vector B for each pixel (pixel of interest PI') in the current subject image CSC is calculated. In FIG. 5, the direction (motion direction) in the motion vector B is represented by an arrow, and a size of the motion vector B (motion amount (first motion amount)) is represented by a length of an arrow. The motion vector B represented by a point indicates that the motion amount (first motion amount) is zero.

The second motion amount calculation processing is different from the first motion amount calculation processing only in that the processing target is changed from the first processing target (immediately previous subject image CSB and current subject image CSC) to the second processing target (immediately previous fluorescent image CFB (FIG. 4) and current fluorescent image CFC (FIGS. 4 and 5)).

The first and second motion amount calculation processing are not limited to the block matching method described above, and other methods (for example, a gradient method) may be used.

In the current subject image CSC, the NR processing unit 923 applies a time filter to an area other than the motion area specified by the control unit 94 and applies a spatial filter to the motion area to perform noise reduction (NR) processing of removing random noise from the current subject image CSC. Similarly, in the current fluorescent image CFC, the NR processing unit 923 applies the time filter to the area other than the motion area specified by the control unit 94 and applies the spatial filter to the motion area to perform the noise reduction (NR) processing of removing random noise from the current fluorescent image CFC.

The superimposed image generation unit 924 generates a superimposed image by superimposing, between corresponding areas (pixels) in all the regions, the subject image and the fluorescent image which are subjected to the NR processing and are consecutive in time series. Then, the superimposed image generation unit 924 outputs the superimposed image to the display controller 93. When the control unit 94 prohibits the superimposition, the superimposed image generation unit 924 outputs only the subject image subjected to the NR processing as the superimposed image to the display controller 93.

The display controller 93 generates a video signal for display based on the superimposed image output from the superimposed image generation unit 924 under the control of the control unit 94. Then, the display controller 93 outputs the video signal to the display device 7 via the second transmission cable 8.

The control unit 94 is configured using, for example, a CPU or the like, and outputs a control signal via the first to third transmission cables 6, 8, and 10 to control the operations of the light source device 3, the camera head 5, and the display device 7 and control the whole operation of the control device 9. As illustrated in FIG. 2, the control unit 94 includes a light source controller 941, an imaging controller 942, a determination unit 943, a superimposition controller 944, and a notification controller 945.

The light source controller 941 outputs a control signal to the light source device 3 via the third transmission cable 10, and alternately switches the state of the light source device 3 to the first and second light emission states in a time division manner. Here, the first light emission state is a state in which white light is emitted. In addition, the second light emission state is a state in which near-infrared excitation light is emitted.

The imaging controller 942 outputs a control signal to the camera head 5 via the first transmission cable 6 and allows the imaging unit 52 to alternately capture the subject image and the fluorescent image in the imaging unit 52 in synchronization with switching timing of the state of the light source device 3.

The determination unit 943 determines whether or not at least one of the subject and the observation device 100 moves from timing before timing at which one of the subject image and the fluorescent image is captured by imaging unit 52 to the timing. In the first embodiment, the determination unit 943 executes first and second determination processing.

Here, in the first determination processing, the determination unit 943 determines whether or not a motion area exists in the current subject image CSC. The motion area is an area formed of pixels in which among all the regions in the current subject image CSC, the first motion amount calculated by the motion amount calculation unit 922 exceeds a specific threshold. Then, when there is the motion area in the current subject image CSC, the determination unit 943 determines that at least one of the subject and the observation device 100 moves. On the other hand, when there is no motion area in the current subject image CSC, the determination unit 943 determines that any of the subject and the observation device 100 does not move.

In addition, in the second determination processing, the determination unit 943 determines whether or not the motion area exists in the current fluorescent image CFC. The motion area is an area formed of pixels in which among all the regions in the current fluorescent image CFC, the second motion amount calculated by the motion amount calculation unit 922 exceeds a specific threshold. Then, when there is the motion area in the current fluorescent image CFC, the determination unit 943 determines that at least one of the subject and the observation device 100 moves. On the other hand, when there is no motion area in the current fluorescent image CFC, the determination unit 943 determines that any of the subject and the observation device 100 does not move.

When the determination unit 943 determines that at least one of the subject and the observation device 100 moves, the superimposition controller 944 causes the superimposed image generation unit 924 to prohibit the superimposition of the subject image and the fluorescent image in all the regions.

If the determination unit 943 determines that at least one of the subject and the observation device 100 moves, a notification controller 945 notifies the notification unit 96 to notify information indicating the movement.

The input unit 95 is configured using operation devices such as a mouse, a keyboard, and a touch panel, and receives user operations by a user such as a doctor. Then, the input unit 95 outputs an operation signal to the control unit 94 according to the user operation.

The notification unit 96 corresponds to a notification device. The notification unit 96 notifies the information indicating the movement under the control of the notification controller 945. Examples of the notification unit 96 include a light emitting diode (LED) that notifies the information according to lighting or blinking or a color when lighting, a display device that displays the information, a speaker that outputs the information by voice, or the like. In the first embodiment, the notification unit 96 is configured to be provided inside the control device 9 but the notification unit 96 is not limited to this configuration, and may be separately configured from the control device 9.

The storage unit 97 stores a program executed by the control unit 94, information required for the processing of the control unit 94, and the like.

Operation of Control Device

Next, the operation of the control device 9 described above will be described.

Figure 6:
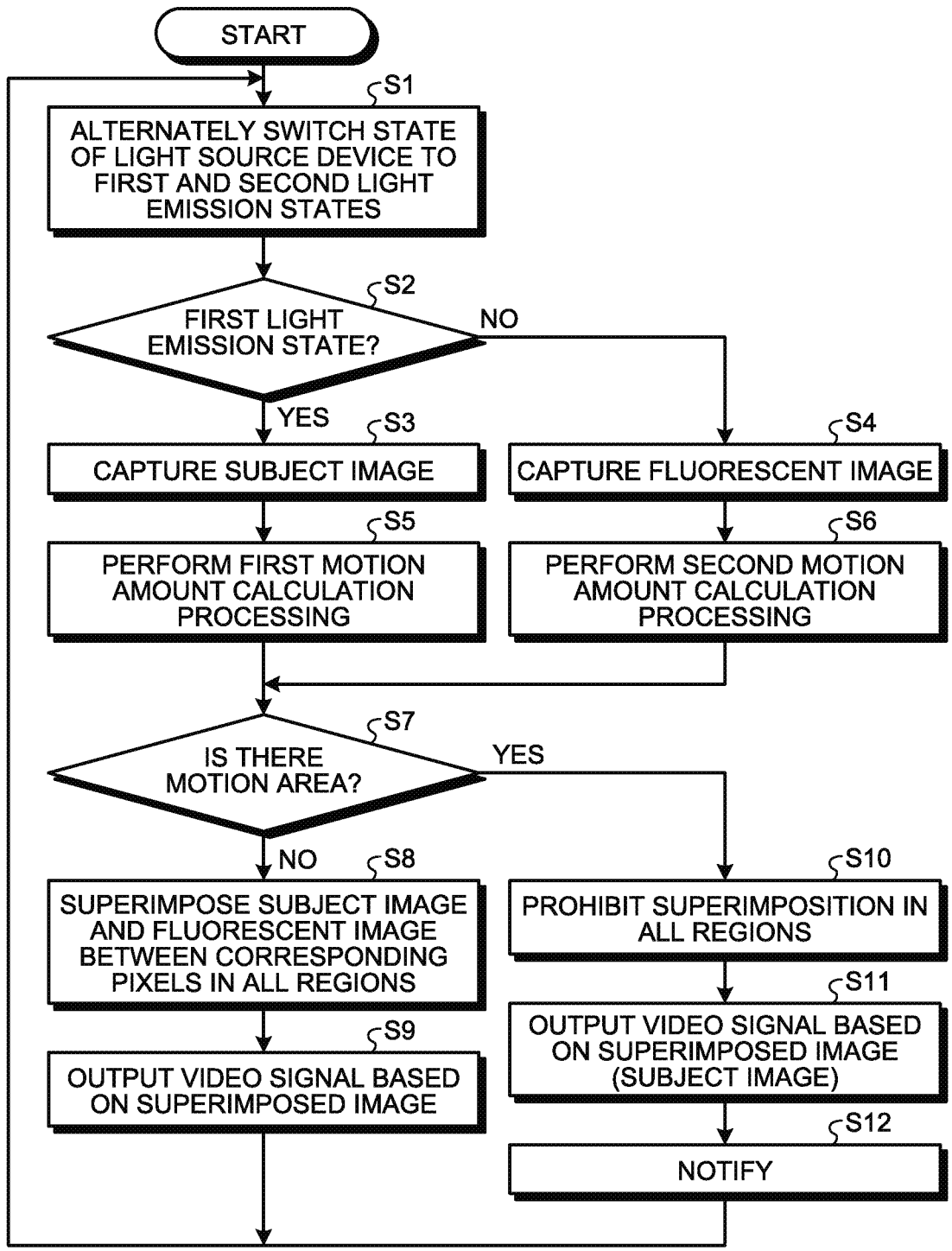
FIG. 6 is a flowchart illustrating an operation of the control device.

FIG. 6 is a flowchart illustrating the operation of the control device 9.

In the following description, a drug such as indocyanine green that is accumulated in a lesion part such as a tumor is previously administered to a subject.

First, the light source controller 941 controls the operation of the light source device 3 and alternately switches the state of the light source device 3 to the first and second light emission states in a time division manner (step S1). Thereby, the white light and the near-infrared excitation light are alternately irradiated to an inside of a living body.

After step S1, the imaging controller 942 causes the imaging unit 52 to alternately capture the subject image and the fluorescent image in synchronization with the switching timing of the state of the light source device 3 (steps S2 to S4). That is, when the state of the light source device 3 is in the first light emission state (step S2: Yes), that is, when the white light is irradiated into the living body, the imaging unit 52 captures the subject image reflected in the living body (step S3). On the other hand, when the state of the light source device 3 is in the second light emission state (step S2: No), that is, when the near-infrared excitation light is irradiated into the living body, the imaging unit 52 excites the drug such as the indocyanine green in the living body and captures the fluorescent image emitted from the inside of the living body (step S4).

When the subject image is captured by the imaging unit 52 (when the current subject image CSC is received by the communication unit 91), the motion amount calculation unit 922 sets the immediately previous subject image CSB and the current subject image CSC as the first processing target and performs the first motion amount calculation processing (step S5).

On the other hand, when the fluorescent image is captured by the imaging unit 52 (when the current fluorescent image CFC is received by the communication unit 91), the motion amount calculation unit 922 sets the immediately previous fluorescent image CFB and the current fluorescent image CFC as the second processing target and performs the second motion amount calculation processing (step S6).

The determination unit 943 executes the first determination processing after step S5, and executes the second determination processing after step S6 (step S7).

As a result of executing the first determination processing, when it is determined that there is no motion area in the current subject image CSC (it is determined that any of the subject and the observation device 100 does not move) (step S7: No), the superimposed image generation unit 924 executes the following processing (step S8).

That is, in step S8, the superimposed image generation unit 924 generates the superimposed image by superimposing, between corresponding pixels in all the regions, the current subject image CSC and the fluorescent image immediately before the current subject image CSC in time series. Then, the superimposed image generation unit 924 outputs the superimposed image to the display controller 93.

As a result of executing the second determination processing, when it is determined that there is no motion area in the current fluorescent image CFC (it is determined that any of the subject and the observation device 100 does not move) (step S7: No), the superimposed image generation unit 924 executes the following processing (step S8).

That is, in step S8, the superimposed image generation unit 924 generates the superimposed image by superimposing, between the corresponding pixels in all the regions, the current fluorescent image CFC and the subject image immediately before the current fluorescent image CFC in time series. Then, the superimposed image generation unit 924 outputs the superimposed image to the display controller 93.

After step S8, the display controller 93 generates the video signal based on the superimposed image output from the superimposed image generation unit 924, and outputs the video signal to the display device 7 (step S9). Thus, the superimposed image is displayed on the display device 7. Thereafter, the control device 9 returns to step S1.

On the other hand, as a result of executing the first determination processing, when it is determined that there is the motion area in the current subject image CSC (it is determined that at least one of the subject and the observation device 100 moves) (step S7: Yes), the superimposition controller 944 causes the superimposed image generation unit 924 to prohibit the superimposition of the subject image and the fluorescent image in all the regions (step S10). Then, the superimposed image generation unit 924 outputs the current subject image CSC as the superimposed image to the display controller 93.

In addition, as a result of executing the second determination processing, similar to the case where it is determined that there is the motion area in the current fluorescent image CFC (it is determined that at least one of the subject and the observation device 100 does not move) (step S7: Yes), the superimposition controller 944 executes the step S10. Then, the superimposed image generation unit 924 outputs, to the display controller 93, the subject image immediately before the current fluorescent image CFC in time series as the superimposed image.

After step S10, the display controller 93 generates the video signal based on the superimposed image (subject image) output from the superimposed image generation unit 924, and outputs the video signal to the display device 7 (step S11). Thus, the subject image is displayed on the display device 7.

After step S11, the notification controller 925 causes the notification unit 96 to notify the information indicating the movement (step S12). Thereafter, the control device 9 returns to step S1.

Specific Example of Displayed Image

Next, a specific example of the image displayed on the display device 7 will be described.

Figure 7:
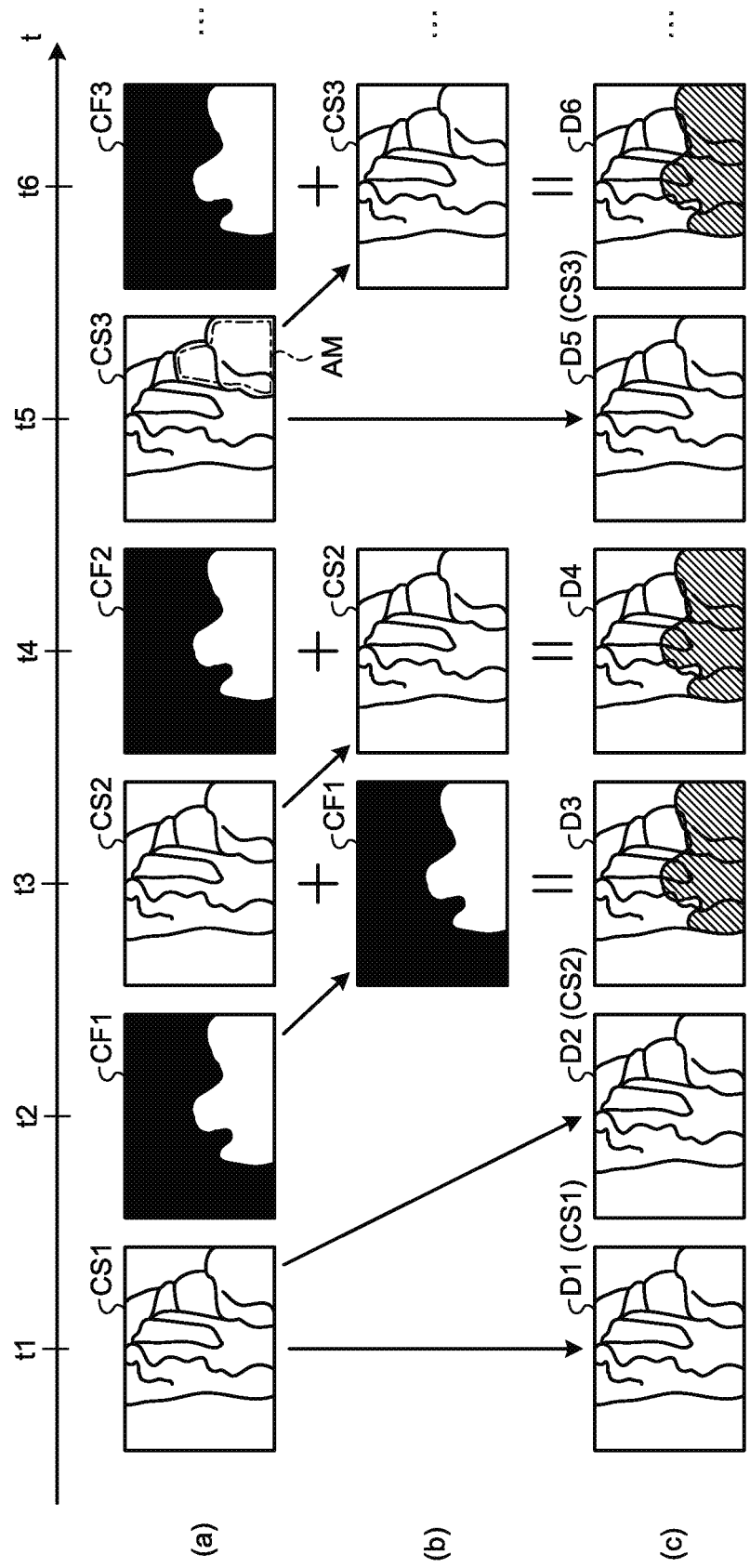
FIG. 7 is a diagram illustrating a concrete example of an image displayed on a display device.

FIG. 7 is a diagram illustrating a specific example of the image displayed on the display device 7. Specifically, a part (a) of FIG. 7 is a view illustrating subject images CS1 to CS3 and fluorescent images CF1 to CF3 captured by the camera head 5 at each timing t1 to t6 arranged in time series. A part (b) of FIG. 7 is a diagram illustrating one of the subject image and the fluorescent image to be superimposed by the superimposed image generation unit 924. A part (c) of FIG. 7 is a diagram illustrating the image displayed on the display device 7.

In FIG. 7, for convenience of description, a mask area MA is not illustrated in the images CS1 to CS3, CF1 to CF3, and D1 to D6. Further, in the fluorescent images CF1 to CF3, the excitation region in which a drug such as indocyanine green in a living body is excited is represented in white, and the area other than the excitation region is represented in black. In addition, in the superimposed images D3, D4, and D6, the excitation regions are represented by an oblique line.

If the image captured by the camera head 5 is a subject image CS1 (current subject image CSC) at initial timing t1 after the activation of the medical observation system 1, there is no subject image (immediately previous subject image CSB) immediately before the subject image CS1 in time series. That is, the motion amount calculation unit 922 cannot perform the first motion amount calculation processing. Then, the superimposed image generation unit 924 outputs the subject image CS1 as the superimposed image D1 to the display controller 93. Thereafter, the display controller 93 generates a video signal based on the superimposed image D1 (subject image CS1), and outputs the video signal to the display device 7. As a result, as illustrated in the part (c) of FIG. 7, the superimposed image D1 (subject image CS1) is displayed on the display device 7 at timing t1.

At timing t2 next to the timing t1, the image captured by the camera head 5 is the fluorescent image CF1 (current fluorescent image CFC). Similar to the timing t1, even in the timing t2, there is no fluorescent image (immediately previous fluorescent image CFB) immediately before the fluorescent image CF1 in time series. That is, the motion amount calculation unit 922 cannot perform the second motion amount calculation processing. Then, the superimposed image generation unit 924 outputs, to the display controller 93, the subject image CS1 immediately before the fluorescent image CF1 in time series as the superimposed image D2. Thereafter, the display controller 93 generates a video signal based on the superimposed image D2 (subject image CS1), and outputs the video signal to the display device 7. As a result, as illustrated in the part (c) of FIG. 7, the superimposed image D2 (subject image CS1) is displayed on the display device 7 at timing t2.

At timing t3 next to the timing t2, the image captured by the camera head 5 is the subject image CS2 (current subject image CSC). At the timing t3, the motion amount calculation unit 922 performs the first motion amount calculation processing on, as the first processing target, the subject image CS2 (current subject image CSC) and the subject image CS1 (immediately previous subject image CSB) immediately before the subject image CS2 in time series (step S5). Here, there is no motion area in the subject image CS2 (current subject image CSC). Therefore, in the first determination processing (step S7), it is determined as "No". Then, the superimposed image generation unit 924 generates a superimposed image D3 by superimposing, between the corresponding pixels in all the regions, the subject image CS2 (current subject image CSC) and the fluorescent image CF1 (the part (b) of FIG. 7) immediately before the subject image CS2 in time series and outputs the superimposed image D3 to the display controller 93 (step S8). Thereafter, the display controller 93 generates a video signal based on the superimposed image D3, and outputs the video signal to the display device 7 (step S9). As a result, as illustrated in the part (c) of FIG. 7, the superimposed image D3 is displayed on the display device 7 at timing t3.

At timing t4 next to the timing t3, the image captured by the camera head 5 is the fluorescent image CF2 (current fluorescent image CFC). At the timing t4, the motion amount calculation unit 922 performs the second motion amount calculation processing on, as the second processing target, the fluorescent image CF2 (current fluorescent image CFC) and the fluorescent image CF1 (immediately previous fluorescent image CFB) immediately before the fluorescent image CF2 in time series (step S6). Here, there is no motion area in the fluorescent image CF2 (current fluorescent image CFC). Therefore, in the second determination processing (step S7), it is determined as "No". Then, the superimposed image generation unit 924 generates a superimposed image D4 by superimposing, between the corresponding pixels in all the regions, the fluorescent image CF2 (current fluorescent image CFC) and the subject image CS2 (the part (b) of FIG. 7) immediately before the fluorescent image CF2 in time series and outputs the superimposed image D4 to the display controller 93 (step S8). Thereafter, the display controller 93 generates a video signal based on the superimposed image D4, and outputs the video signal to the display device 7 (step S9). As a result, as illustrated in the part (c) of FIG. 7, the superimposed image D4 is displayed on the display device 7 at timing t4.

At timing t5 next to the timing t4, the image captured by the camera head 5 is a subject image CS3 (current subject image CSC). At the timing t5, the motion amount calculation unit 922 performs the first motion amount calculation processing, as the first processing target, the subject image CS3 (current subject image CSC) and the subject image CS2 (immediately previous subject image CSB) immediately before the subject image CS3 in time series (step S5). Here, a motion area AM (the part (a) of FIG. 7) exists in the subject image CS3 (current subject image CS3). Therefore, in the first determination processing (step S7), it is determined as "Yes". Then, the superimposition controller 944 causes the superimposed image generation unit 924 to prohibit the superimposition of the subject image and the fluorescent image in all the regions (step S10). In addition, the superimposed image generation unit 924 outputs the subject image CS3 as the superimposed image D5 to the display controller 93. Thereafter, the display controller 93 generates a video signal based on the superimposed image D5 (subject image CS3), and outputs the video signal to the display device 7 (step S11). As a result, as illustrated in the part (c) of FIG. 7, the superimposed image D5 (subject image CS3) is displayed on the display device 7 at timing t5. In addition, the notification unit 96 notifies the information indicating the movement (step S12).

At timing t6 next to the timing t5, the image captured by the camera head 5 is a fluorescent image CF3 (current fluorescent image CFC). At the timing t6, the motion amount calculation unit 922 performs the second motion amount calculation processing on, as the second processing target, the fluorescent image CF3 (current fluorescent image CFC) and the fluorescent image CF2 (immediately previous fluorescent image CFB) immediately before the fluorescent image CF3 in time series (step S6). Here, there is no motion area in the fluorescent image CF3 (current fluorescent image CFC). Therefore, in the second determination processing (step S7), it is determined as "No". Then, the superimposed image generation unit 924 generates a superimposed image D6 by superimposing, between the corresponding pixels in all the regions, the fluorescent image CF3 (current fluorescent image CFC) and the subject image CS3 (the part (b) of FIG. 7) immediately before the fluorescent image CF3 in time series and outputs the superimposed image D6 to the display controller 93 (step S8). Thereafter, the display controller 93 generates a video signal based on the superimposed image D6, and outputs the video signal to the display device 7 (step S9). As a result, as illustrated in the part (c) of FIG. 7, the superimposed image D6 is displayed on the display device 7 at timing t6. In addition, the notification unit 96 stops the information indicating the movement.

According to the first embodiment described above, the following effects are obtained.

The control device 9 according to the first embodiment determines whether or not at least one of the subject and the observation device 100 moves from timing before timing at which one of the subject image and the fluorescent image is captured to the timing. Then, when it is determined that both the subject and the observation device 100 do not move, the control device 9 generates the superimposed image by superimposing the subject image and the fluorescent image between the corresponding pixels in all the regions. On the other hand, when it is determined that at least one of the subject and the observation device 100 moves, the control device 9 does not superimpose the subject image and the fluorescent image.

Therefore, even when at least one of the subject and the observation device 100 moves, the display device 7 does not display the superimposed image in which the corresponding observed regions of the subject image and the fluorescent image are shifted from each other. That is, there is a possibility that the doctor does not recognize, as a lesion part, a site at which no lesion part is actually present, from the superimposed image displayed on the display device 7. Therefore, according to the control device 9 according to the first embodiment, the convenience may be improved.

Further, the control device 9 according to the first embodiment determines, based on the first and second motion amounts calculated in the first and second motion amount calculation processing, whether or not at least one of the subject and the observation device 100 moves.

That is, since the determination on whether or not at least one of the subject and the observation device 100 moves may be executed by the image processing of the subject image or the fluorescent image, the observation device 100 does not need to be equipped with devices such as an acceleration sensor or a gyro sensor. Therefore, the structure of the medical observation system 1 may be simplified.

In particular, in the first motion amount calculation processing, two subject images are set as the first processing target. In addition, similarly in the second motion amount calculation processing, two fluorescent images are set as the second processing target.

Therefore, for example, compared with the configuration in which the motion amount calculation processing is performed on the subject image and the fluorescent image, the motion amount may be calculated with high accuracy, and it is possible to determine whether or not at least one of the subject and the observation device 100 moves with high accuracy.

Further, in the control device 9 according to the first embodiment, the first processing target used in the first motion amount calculation processing is set as two subject images consecutive in time series. In addition, the second processing target used in the second motion amount calculation processing is set as two fluorescent images consecutive in time series.

Therefore, it is possible to appropriately determine whether or not at least one of the subject and the observation device 100 moves from timing immediately before the timing at which the current subject image CSC or the current fluorescent image CFC is captured to the timing.

Further, in the first embodiment, the observation device 100 alternately captures the subject image and the fluorescent image to alternately generate the subject image and the fluorescent image sequentially. In addition, the control device 9 superimposes the subject image and the fluorescent image which are consecutive in time series to generate the superimposed image.

Therefore, the same superimposed image is not consecutively displayed for each frame, and the superimposed image (superimposed images D3 to D6 in the example of FIG. 7) obtained by capturing the latest state of the subject may be sequentially displayed for each frame.

Here, the subject image is an image obtained by irradiating the subject with white light and capturing the subject image reflected from the subject. Therefore, the subject image is an image that is easy to recognize the entire shape of a subject's mucosa and the like. On the other hand, the fluorescent image is an image obtained by irradiating the subject with near-infrared excitation light, exciting a drug such as indocyanine green accumulated in a lesion part in the subject, and capturing the fluorescent image emitted from the subject. Therefore, the fluorescent image is an image that is hard to recognize the entire shape of a subject's mucosa and the like.

Here, in the medical observation system 1 according to the first embodiment, when it is determined that at least one of the subject image and the observation device 100 moves, the subject image is displayed on the display device 7.

That is, when at least one of the subject and the observation device 100 moves, the image displayed on the display device 7 does not disappear, and the subject image that easily recognizes the entire shape of the subject's mucosa or the like is displayed on the display device 7. Therefore, a doctor may continuously check the state of the subject. Therefore, it is possible to further improve the convenience.

In addition, when it is determined that at least one of the subject and the observation device 100 moves, the control device 9 according to the first embodiment notifies the notification unit 96 of the information indicating the movement.

For this reason, when the display is switched from the immediately previous superimposed image (superimposed image D4 in the example of FIG. 7) to the current superimposed image (superimposed image D5 in the example of FIG. 7), a doctor and the like may recognize, based on the information, the reason in which the excitation region (represented by a diagonal line in the example of FIG. 7) disappears.

Therefore, it is possible to improve the convenience.

Second Embodiment

Next, a second embodiment will be described.

In the following description, the same reference numerals are given to the same components as those of the above-described first embodiment, and a detailed description thereof will be omitted or simplified.

In the second embodiment, functions of a superimposed image generation unit 924 and a superimposition controller 944 are different from those of the first embodiment described above. The functions of the superimposed image generation unit 924 and the superimposition controller 944 according to the second embodiment will be described in the following "operation of control device 9".

Operation of Control Device

Figure 8:
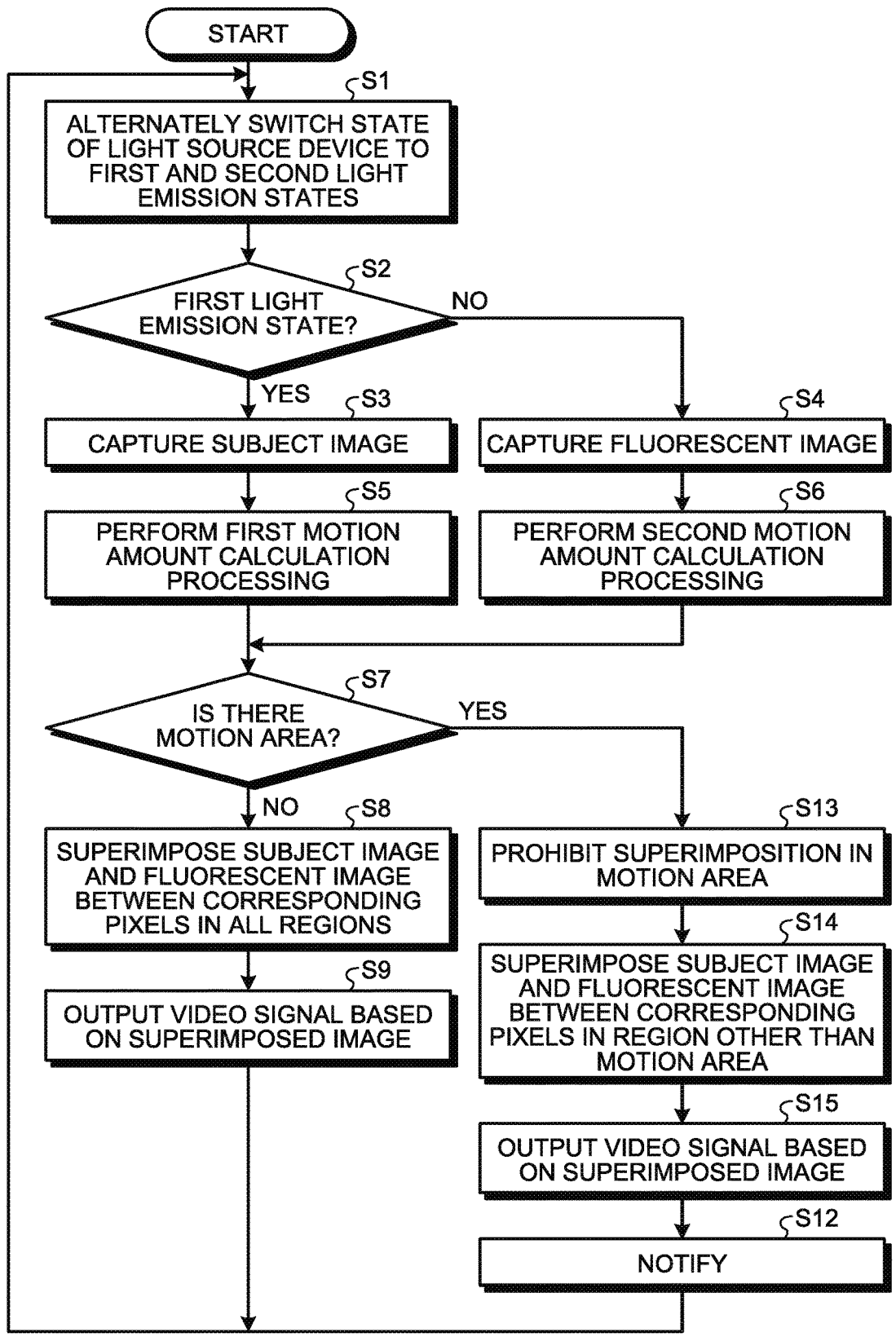
FIG. 8 is a flowchart illustrating an operation of a control device according to a second embodiment.

FIG. 8 is a flowchart illustrating an operation of a control device 9 according to the second embodiment.

In the operation of the control device 9 according to the second embodiment, as illustrated in FIG. 8, steps S13 to S15 are performed instead of steps S10 and S11 with respect to the operation of the control device 9 described in the first embodiment described above. For this reason, only steps S13 to S15 will be described below.

As a result of performing the first determination processing, if it is determined that there is the motion area in the current subject image CSC (step S7: Yes), the superimposition controller 944 causes the superimposed image generation unit 924 to prohibit the superimposition in the motion area of the subject image and the fluorescent image, and permit the superimposition in an area other than the motion area (step S13). Thereafter, the superimposed image generation unit 924 generates the superimposed image by superimposing, between corresponding pixels in the area other than the motion area, the subject image CSC and the fluorescent image immediately before the current subject image CSC in time series (step S14). In the superimposed image, the region (motion area) whose superimposition is prohibited by the superimposition controller 944 is configured by a corresponding area in the current subject image CSC. Then, the superimposed image generation unit 924 outputs the superimposed image to the display controller 93.

In addition, as a result of executing the second determination processing, similar to the case where it is determined that there is the motion area in the current fluorescent image CFC (step S7: Yes), the superimposition controller 944 executes the step S13. Thereafter, the superimposed image generation unit 924 generates the superimposed image by superimposing, between corresponding pixels in the area other than the motion area, the current fluorescent image CFC and the subject image immediately before the current fluorescent image CFC in time series (step S14). In the superimposed image, the region (motion area) whose superimposition is prohibited by the superimposition controller 944 is configured by a corresponding area in the immediately previous current subject image to the current fluorescent image CFC in time series. Then, the superimposed image generation unit 924 outputs the superimposed image to the display controller 93.

After step S14, the display controller 93 generates the video signal based on the superimposed image output from the superimposed image generation unit 924, and outputs the video signal to the display device 7 (step S15). Thus, the superimposed image is displayed on the display device 7. Thereafter, the control device 9 performs step S12.

Specific Example of Displayed Image

Next, a specific example of the image displayed on the display device 7 will be described.

FIG. 9 is a diagram illustrating a specific example of the image displayed on the display device 7. FIG. 9 is a diagram corresponding to FIG. 7. Further, in the superimposed image D5, similarly to the superimposed images D3, D4, and D6, an excitation region in which a drug such as indocyanine green in a living body is excited is represented by a diagonal line.

Hereinafter, at each timing t1 to t6 arranged in time series, the case where subject images CS1 to CS3 and fluorescent images CF1 to CF3 identical to the image (the part (a) of FIG. 7) described in the first embodiment described above are captured by a camera head 5 will be described.

Compared with the first embodiment described above, in the second embodiment, different images are displayed only at timing t5. For this reason, only the timing t5 will be described below.

At the timing t5, the image captured by the camera head 5 is the subject image CS3 (current subject image CSC). At the timing t5, the motion amount calculation unit 922 performs the first motion amount calculation processing, as the first processing target, the subject image CS3 (current subject image CSC) and the subject image CS2 (immediately previous subject image CSB) immediately before the subject image CS3 in time series (step S5). Here, a motion area AM (a part (a) of FIG. 9) exists in the subject image CS3 (current subject image CS3). Therefore, in the first determination processing (step S7), it is determined as "Yes". Then, the superimposition controller 944 causes the superimposed image generation unit 924 to prohibit the superimposition in the motion area AM of the subject image and the fluorescent image (step S13). In addition, the superimposed image generation unit 924 generates a superimposed image D5 by superimposing, between the corresponding pixels in the area other than the motion area AM, the subject image CS3 (current subject image CSC) and the fluorescent image CF2 immediately before the subject image CS3 in time series and outputs the superimposed image D5 to the display controller 93 (step S14). In the superimposed image D5, the motion area AM is configured by the corresponding area in the current subject image CS3. Thereafter, the display controller 93 generates a video signal based on the superimposed image D5, and outputs the video signal to the display device 7 (step S15). As a result, as illustrated in a part (c) of FIG. 9, the superimposed image D5 is displayed on the display device 7 at timing t5. In addition, the notification unit 96 notifies the information indicating the movement (step S12).

If it is determined that at least one of the subject and the observation device 100 moves as in the second embodiment described above, even in the case of the configuration in which the superimposition of the subject image and the fluorescent image in the motion area is prohibited and the superimposition in the area other than the motion area is permitted, the same effects as those in the first embodiment are obtained.

Other Embodiments

Although the embodiments for carrying out the present disclosure have been described so far, the present disclosure should not be limited only to the first and second embodiments described above.

The above-described embodiments 1 and 2 determine based on the first and second motion amounts calculated by the first and second motion amount calculation processing whether or not at least one of the subject and the observation device 100 moves, but are not limited thereto. For example, a device such as an acceleration sensor or a gyro sensor is mounted on the observation device 100, and it is determined based on the acceleration or angular velocity detected by the device such as the acceleration sensor or the gyro sensor whether or not the observation device 100 moves.

In the first and second embodiments described above, the first and second motion amounts are calculated by the block matching method or the gradient method, but the first and second embodiments are not limited thereto.

For example, pixel levels of two subject images captured at different timings are compared between the corresponding pixels. Then, the change amount of the pixel level may be calculated as the first motion amount. Similarly, the pixel levels of two fluorescent images captured at different timings are compared between the corresponding pixels. Then, the change amount of the pixel level may be calculated as the second motion amount. At this time, instead of the configuration in which the first and second motion amounts may each be calculated for each pixel, the first and second motion amounts may each be calculated for each pixel group (area) including a plurality of pixels. The same applies to the first and second embodiments described above.

Note that, as the pixel level, if the subject image or the fluorescent image is an image before demosaic processing, component information (pixel value) of any of read (R), green (G), and blue (B) corresponding to each filter group of R, G, and B constituting a color filter provided on the imaging surface of the image sensor (imaging unit 52) may be exemplified. Further, as the pixel level, if the subject image or the fluorescent image is an image after the demosaic processing, a luminance value according to the RGB value (pixel value) or a Y signal (luminance signal) may be exemplified.

In the first and second embodiments described above, the same type of two subject images or the same type of two fluorescent images are adopted as processing targets used in the motion amount calculation processing, but the first and second embodiments are not limited thereto, and the subject image and the fluorescent image may be adopted as the processing targets. That is, the motion amount may be calculated by comparing the subject image with the fluorescent image.

In the first and second embodiments described above, although two subject images consecutive in time series are set to the first processing target, the first and second embodiments are not limited thereto, and two subject images not consecutive in time series may be set to the first processing target. That is, the current subject image CSC and the subject image captured by the camera head 5 four frames before with respect to the current subject image CSC may be adopted as the first processing target.

Similarly, in the first and second embodiments described above, although two fluorescent images consecutive in time series are set to the second processing target, the first and second embodiments are not limited thereto, and two fluorescent images not consecutive in time series may be set to the second processing target. That is, the current fluorescent image CFC and the fluorescent image captured by the camera head 5 four frames before with respect to the current fluorescent image CFC may be adopted as the second processing target.

In the first and second embodiments described above, a configuration may be adopted in which only one of the first and second motion amount calculation processing (first and second determination processing) is performed.

In the first and second embodiments described above, when the subject image and the fluorescent image are superimposed, the current subject image CSC and the fluorescent image immediately before the current subject image CSC in time series are superimposed, but the first and second embodiments are not limited thereto. For example, the current subject image CSC and the fluorescent image immediately after the current subject image CSC in time series may be superimposed.

Similarly, in the first and second embodiments described above, when the subject image and the fluorescent image are superimposed, the current fluorescent image CFC and the subject image immediately before the current fluorescent image CFC in time series are superimposed, but the first and second embodiments are not limited thereto. For example, the current fluorescent image CFC and the subject image immediately after the current fluorescent image CFC in time series may be superimposed.

In the first and second embodiments described above, the subject image and the fluorescent image are alternately captured, and the subject image and the fluorescent image are alternately generated for each frame, but the first and second embodiments are not limited thereto. For example, a configuration may be adopted in which at least one of the subject image and the fluorescent image is consecutively captured, and at least one of the subject image and the fluorescent image is consecutively generated for several frames.

In the first and second embodiments described above, step S12 may be omitted. Further, in the first and second embodiments described above, steps S8, S9, and S12 may be performed when "Yes" is determined in step S7.

In the first and second embodiments described above, the configuration of the light source device 3 is not limited to the configuration described in the first and second embodiments described above, and in the case of a configuration capable of emitting the white light and the near-infrared excitation light in a time division manner, other configurations may be adopted.

Similarly, in the first and second embodiments described above, the configuration of the imaging unit 52 is not limited to the configuration described in the first and second embodiments described above, and in the case of a configuration capable of generating the subject image and the fluorescent image, the configuration using two image sensors may be adopted.

In the first and second embodiments described above, the white light is used when generating the subject image, but the first and second embodiments are not limited thereto, and light in another specific wavelength band may be adopted.

Similarly, in the first and second embodiments described above, the near-infrared excitation light is used when generating the fluorescent image, but the first and second embodiments are not limited thereto, and light in another specific wavelength band may be adopted.

In the first and second embodiments described above, the medical image processing apparatus is mounted on the medical observation system 1 in which the insertion unit 2 is constituted by a rigid endoscope, but the first and second embodiments are not limited thereto. For example, the medical image processing apparatus may be mounted on the medical observation system in which the insertion unit 2 is constituted by a flexible endoscope. In addition, the medical image processing apparatus may be mounted on the medical observation system such as a surgical microscope (for example, see JP 2016-42981 A) for enlarging and observing a predetermined visual field area in a subject (in a living body) or a subject surface (surface of a living body).

In the first and second embodiments described above, the configuration of a part of the camera head 5 or the configuration of a part of the control device 9 may be provided in, for example, the connector CN1 or the connector CN2.

According to the medical image processing apparatus and the medical observation system, the convenience may be improved.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical image processor connected to an observation imager that generates a subject image by capturing the subject image reflected from a subject at a first timing and generates a fluorescent image by capturing a fluorescent image emitted from the subject at a second timing, different from the first timing, from the subject image, the medical image processor comprising circuitry configured to:
   determine whether or not at least one of the subject and the observation imager moves between the first timing and a subject image at a first previous timing or between the second timing and a fluorescent image at a second previous timing; and
   generate an output image by superimposing the subject image and the fluorescent image on condition that motion did not occur in an area and prohibiting a superimposition in an area of at least a part of the subject image and the fluorescent image when at least one of the subject and the observation imager moves.

2. The medical image processor according to claim 1, wherein the observation imager sequentially generates the subject image by capturing the subject image at different timings and sequentially generates the fluorescent image by capturing the fluorescent image at different timings, the circuitry is configured to:

set two subject images generated by the observation imager to a first processing target, set two fluorescent images generated by the observation imager to a second processing target, perform first motion amount calculation processing of calculating a first motion amount from a first subject image for each area to a second subject image and second motion amount calculation processing of calculating a second motion amount from a first fluorescent image for each area to a second fluorescent image, and perform first determination processing of determining based on the first motion amount whether or not at least one of the subject and the observation imager moves and second determination processing of determining based on the second motion amount whether or not at least one of the subject and the observation imager moves.

3. The medical image processor according to claim 2, wherein the first processing target is the two subject images consecutive in time series, and the second processing target is the two fluorescent images consecutive in time series.

4. The medical image processor according to claim 3, wherein the observation imager alternatively generates the subject image and the fluorescent image sequentially by alternately capturing the subject image and the fluorescent image, the circuitry is configured to:

generate the superimposed image by superimposing the subject image and the fluorescent image consecutive in time series.

5. The medical image processor according to claim 2, wherein in the first determination processing, when a motion area in which the first motion amount exceeds a specific threshold value exists in the subject image, the circuitry is configured to determine that at least one of the subject and the observation imager moves, and in the second determination processing, when a motion area in which a second motion amount exceeds a specific threshold value exists in the fluorescent image, the circuitry is configured to determine that at least one of the subject and the observation imager moves.

6. The medical image processor according to claim 5, wherein the circuitry is configured to prohibit the superimposition in the motion area of the subject image and the fluorescent image and permit the superimposition in an area other than the motion area when at least one of the subject and the observation imager moves.

7. The medical image processor according to claim 5, wherein the circuitry is configured to prohibit the superimposition of the subject image and the fluorescent image when at least one of the subject and the observation imager moves.

8. The medical image processor according to claim 1, wherein the circuitry is configured to generate the output image by setting an area where the superimposition is prohibited to the corresponding area in the subject image.

9. A medical observation system, comprising:

an observation imager configured to generate a subject image by capturing the subject image reflected from a subject and generate a fluorescent image by capturing a fluorescent image emitted from the subject at different timing from the subject image;

the medical image processor according to claim 1 that is connected to the observation imager and processes the subject image and the fluorescent image; and a display configured to display a superimposed image generated by the medical image processor.

10. A medical image processor connected to an observation imager that generates a subject image by capturing the subject image reflected from a subject at a first timing and generates a fluorescent image by capturing a fluorescent image emitted from the subject at a second timing, different from the first timing, the medical image processor comprising circuitry configured to:

determine whether or not at least one of the subject and the observation imager moves between the first timing and a subject image at a first previous timing or between the second timing and a fluorescent image at a second previous timing;

generate an output image by superimposing the subject image and the fluorescent image on condition that motion did not occur in an area and prohibiting a superimposition in an area of at least a part of the subject image and the fluorescent image when at least one of the subject and the observation imager moves; and notify a notification device of information indicating motion when at least one of the subject and the observation imager moves.

11. A medical observation system, comprising:

an observation imager configured to generate a subject image by capturing the subject image reflected from a subject and generate a fluorescent image by capturing a fluorescent image emitted from the subject at different timing from the subject image;

the medical image processor according to claim 10 that is connected to the observation imager and processes the subject image and the fluorescent image; and a display configured to display a superimposed image generated by the medical image processor.

12. The medical image processor according to claim 10, wherein the observation imager sequentially generates the subject image by capturing the subject image at different timings and sequentially generates the fluorescent image by capturing the fluorescent image at different timings, the circuitry is configured to:

set two subject images generated by the observation imager to a first processing target, set two fluorescent images generated by the observation imager to a second processing target, perform first motion amount calculation processing of calculating a first motion amount from a first subject image for each area to a second subject image and second motion amount calculation processing of calculating a second motion amount from a first fluorescent image for each area to a second fluorescent image, and perform first determination processing of determining based on the first motion amount whether or not at least one of the subject and the observation-imager moves and second determination processing of determining based on the second motion amount whether or not at least one of the subject and the observation-imager moves.

13. The medical image processor according to claim 12, wherein
the first processing target is the two subject images consecutive in time series, and
the second processing target is the two fluorescent images consecutive in time series.

14. A medical image processor connected to an observation imager that generates a subject image by capturing the subject image reflected from a subject at a first timing and generates a fluorescent image by capturing a fluorescent image emitted from the subject at a second timing, different from the first timing, from the subject image, the medical image processor comprising circuitry configured to:
determine whether or not at least one of the subject and the observation imager moves between the first timing and a subject image at a first previous timing or between the second timing and a fluorescent image at a second previous timing;
generate an output image by superimposing the subject image and the fluorescent image on condition that motion did not occur in an area and prohibiting a superimposition in an area of at least a part of the subject image and the fluorescent image when at least one of the subject and the observation imager moves; and
control the output image based on a result of the determination.

15. The medical image processor according to claim 14, wherein
the observation imager sequentially generates the subject image by capturing the subject image at different timings and sequentially generates the fluorescent image by capturing the fluorescent image at different timings,
the circuitry is configured to:
set two subject images generated by the observation imager to a first processing target,
set two fluorescent images generated by the observation imager to a second processing target,
perform first motion amount calculation processing of calculating a first motion amount from a first subject image for each area to a second subject image and second motion amount calculation processing of calculating a second motion amount from a first fluorescent image for each area to a second fluorescent image, and
perform first determination processing of determining based on the first motion amount whether or not at least one of the subject and the observation imager moves and second determination processing of determining based on the second motion amount whether or not at least one of the subject and the observation imager moves.

16. The medical image processor according to claim 15, wherein
the first processing target is the two subject images consecutive in time series, and
the second processing target is the two fluorescent images consecutive in time series.

17. The medical image processor according to claim 16, wherein
the observation imager alternatively generates the subject image and the fluorescent image sequentially by alternately capturing the subject image and the fluorescent image,
the circuitry is configured to:
generate the output image by using the subject image and the fluorescent image consecutive in time series.

18. The medical image processor according to claim 15, wherein
in the first determination processing, when a motion area in which the first motion amount exceeds a specific threshold value exists in the subject image, the circuitry is configured to determine that at least one of the subject and the observation imager moves, and
in the second determination processing, when a motion area in which a second motion amount exceeds a specific threshold value exists in the fluorescent image, the circuitry is configured to determine that at least one of the subject and the observation imager moves.

19. A medical observation system, comprising:
an observation imager configured to generate a subject image by capturing the subject image reflected from a subject and generate a fluorescent image by capturing a fluorescent image emitted from the subject at different timing from the subject image;
determine whether or not at least one of the subject and the observation imager moves between the first timing and a subject image at a first previous timing or between the second timing and a fluorescent image at a second previous timing; and
the medical image processor according to claim 14 that is connected to the observation imager and processes the subject image and the fluorescent image; and
a display configured to display the output image generated by the medical image processor.

* * * * *